United States Patent [19]

Zaiger

[11] Plant 5,146

[45] Nov. 29, 1983

[54] ALMOND TREE (GARDEN PRINCESS)

[76] Inventor: Chris F. Zaiger, 537 Rosemore Ave., Modesto, Calif. 95351

[21] Appl. No.: 346,607

[22] Filed: Feb. 8, 1982

[51] Int. Cl.[3] ..... A01H 5/03
[52] U.S. Cl. ..... Plt./30
[58] Field of Search ..... Plt./30

*Primary Examiner*—Robert E. Bagwill

[57] ABSTRACT

A new and distinct variety of almond tree which is of small size, upright in growth, being a regular and productive bearer of medium size, soft shell, sweet kernel almonds. The tree is further characterized by having foliage of medium size leaves, an abundance of dark pink bloom, the blooming and harvest time being essentially with Mission Almond (unpatented).

2 Drawing Figures

ORIGIN OF THE VARIETY

The present variety of almond tree was originated by me in my experimental orchard located near Modesto, Calif., from a second generation seedling of a cross between Merced Almond (U.S. Plant Pat. No. 1,730) and a genetic dwarf peach seedling with double red flowers. A selected seedling from the first generation having desirable characteristics, including self fertility, was selfed to give a large number of seedlings from which this new and distinct variety of self-fertile, soft shelled almond was selected.

ASEXUAL REPRODUCTION OF THE VARIETY

The present variety was asexually reproduced by budding, as performed by me at my experimental orchard located near Modesto, Calif. and shows that such reproductions and said characteristics run true to form and are established and transmitted through succeeding propagations.

SUMMARY OF THE VARIETY

The present variety of almond tree is of medium vigor, dense and upright in growth, a regular and heavy bearer of medium size soft shelled sweet kernel almonds; the tree is further characterized by having large showy dark pink bloom giving the appearance of an attractive ornamental that produces sweet kernel almonds which are easy to harvest and hull, the harvest time being essentially with Mission Almond. The variety being self fruitful and also having the ability to serve as an effective pollenizer for other varieties of almonds.

BRIEF DESCRIPTION OF THE DRAWING

The accompanying photographic reproductions in color show typical specimens of the foliage, blossoms, and nuts of my new variety, with upper and lower surface of the foliage being illustrated and a branch with clusters of nuts attached; nuts in the hull, nuts out of hull, but in shell and kernels out of the shell.

DESCRIPTION OF THE VARIETY

The botanical details of the new and distinct variety of almond tree, its foliage and nuts as based upon observations of specimens grown near Modesto, Calif. The color terminology (except those in common terms) in accordance with Reinhold Color Atlas by A. Kornerup and J. H. Wanscher.

Tree:
- *Size.*—Small. Approximately ⅔ height of Merced.
- *Vigor.*—Medium.
- *Density.*—Dense.
- *Production.*—Productive.
- *Bearing.*—Regular.

Trunk:
- *Form.*—Stocky.
- *Texture.*—Medium.

Branches:
- *Form.*—Stocky.
- *Texture.*—Medium.
- *Lenticels.*—Medium number and size.
- *Branching habit.*—Upright.

Leaves:
- *Size.*—Small. Average length — 3¼". Average width — 1".
- *Shape.*—Ovate.
- *Thickness.*—Medium.
- *Texture.*—Smooth.
- *Margin.*—Crenate.
- *Petiole.*—Medium length. Medium thickness.
- *Color.*—Upper surface — Grayish green (28-F-8) to (29-F-8). Lower surface — Dull green (28-E-6) to (28-E-7).
- *Glands.*—Number 2 to 6. Usually two, alternate, primarily on petiole.

Bloom:
- *Amount.*—Heavy.
- *Color.*—Dark pink (12-A-5) to (12-B-6).
- *Blooming period.*—Usually 4 to 5 days after Merced Almond.

Crop:
- *Bearing.*—Regular bearer.
- *Production.*—Heavy.
- *Harvest period.*—Approximately with Mission.

Hull:
- *Outer surface.*—Slightly rough.
- *Suture.*—Ridged.
- *Dehiscence.*—Opens freely.
- *Splitting.*—Along suture.

Nut:
- *Size.*—Average length — 1⅛". Average width — ⅝".
- *Form.*—Length/width — Ovate. Width/thickness — Medium plump.
- *Shell.*—Soft.
- *Color.*—Brownish orange (5-B-5).
- *Pits.*—Small, numerous.

*Base.*—Square to ventrally oblique.
*Apex.*—Acute.
*Wing.*—Broad and thin.
*Percentage of kernel to nut.*—Average 58%.

Kernel:

*Size.*—Average length — $\frac{3}{4}''$. Average width — 7/16".
*Form.*—Length/width — Ovate. Width/thickness — Medium plump.
*Base.*—Usually round, some slightly straight.
*Apex.*—Acuminate. Slightly prolonged at tip.
*Texture.*—Smooth to wrinkled.
*Pellicle.*—Thin.
*Number of doubles.*—Few.
*Flavor.*—Sweet.
*Quality.*—Good.

*Color of skin.*—Orange-yellow (5-B-8).
*Color of meat.*—White (1-A-1).

The tree and its nuts herein described may vary in slight detail due to climatic and soil conditions under which it may be grown; the present description being of the variety grown in my experimental orchard near Modesto, Calif.

The following is claimed:

1. A new and distinct variety of almond tree, as illustrated and described, characterized by the tree being small size, upright in growth, and a heavy regular bearer of medium size, sweet kernel nuts harvesting at the same time as Mission; the tree is further characterized by its heavy set of dark pink bloom, blooming 4 to 5 days after Merced, and being self-fertile.

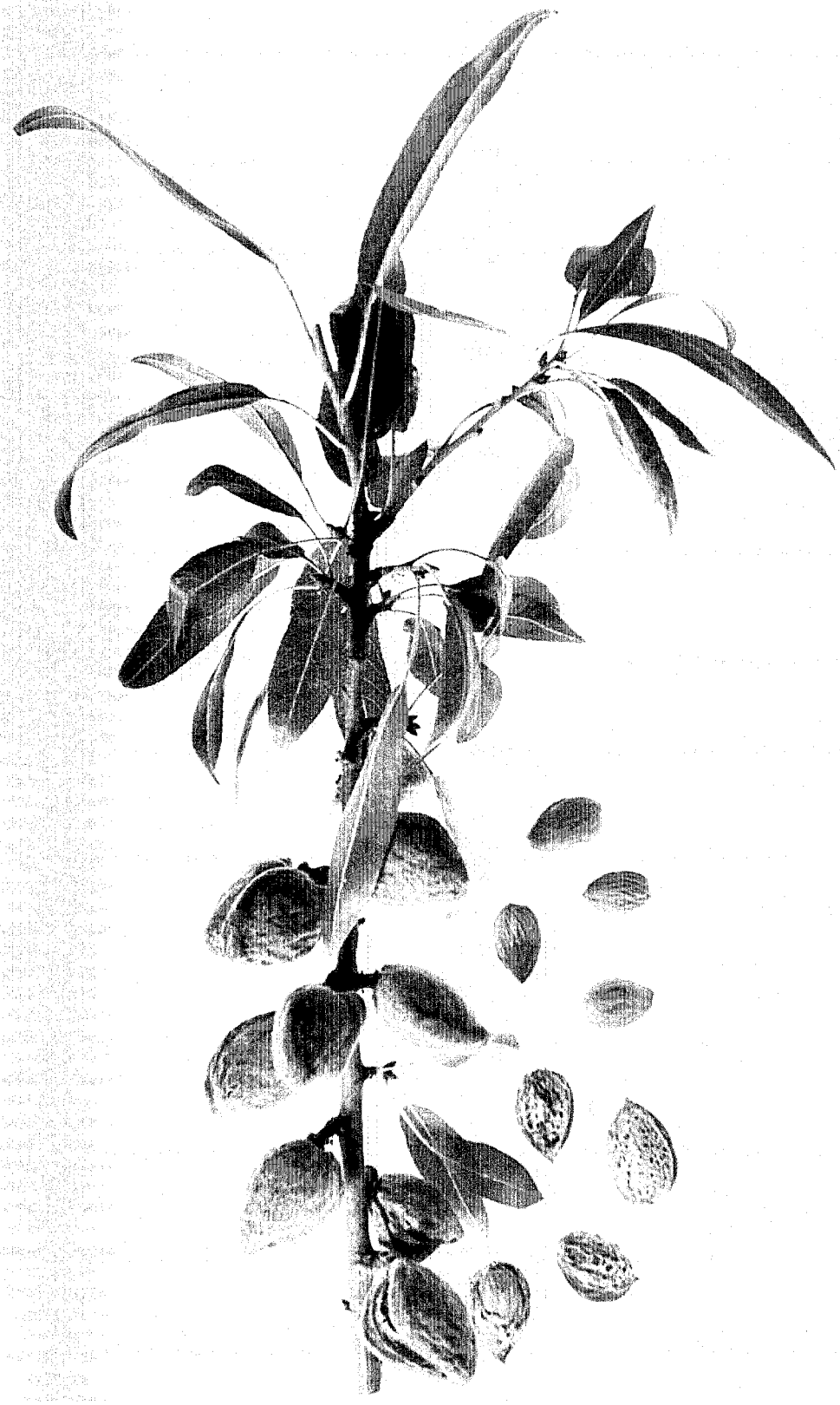

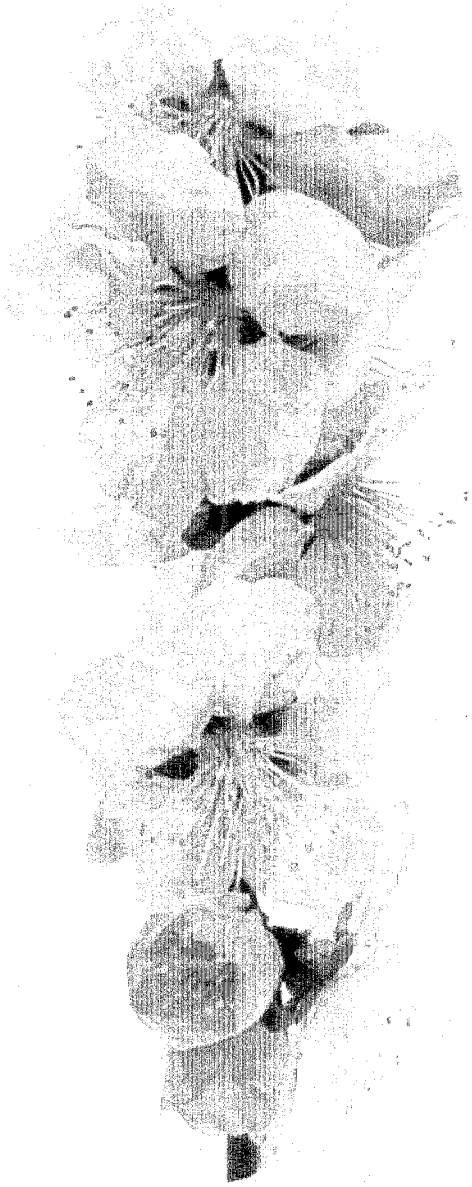

* * * * *